United States Patent [19]

Bafundo et al.

[11] Patent Number: 4,935,007
[45] Date of Patent: Jun. 19, 1990

[54] ANTICOCCIDIAL METHOD

[75] Inventors: Kenneth W. Bafundo, Indianapolis; Thomas K. Jeffers, Greenfield, both of Ind.

[73] Assignee: Eli Lilly and Company, Indianapolis, Ind.

[21] Appl. No.: 284,227

[22] Filed: Dec. 14, 1988

Related U.S. Application Data

[63] Continuation of Ser. No. 901,912, Aug. 28, 1986, abandoned.

[51] Int. Cl.$^5$ ............................................. A61M 31/00
[52] U.S. Cl. ..................................... 604/49; 128/897; 424/88
[58] Field of Search ........................... 424/88, 89, 93; 435/245; 604/49, 54; 600/897, 898

[56] References Cited

U.S. PATENT DOCUMENTS

| | | |
|---|---|---|
| 3,147,186 | 4/1961 | Edgar ..................................... 424/88 |
| 4,301,148 | 11/1981 | Shibata et al. ........................ 424/88 |
| 4,438,097 | 3/1984 | Shirley .................................. 424/93 |
| 4,458,630 | 7/1984 | Sharma et al. . |
| 4,468,380 | 8/1984 | O'Doherty et al. ................. 514/598 |
| 4,526,997 | 7/1985 | O'Doherty et al. .................. 564/50 |
| 4,544,548 | 10/1985 | Davis et al. ........................... 424/93 |
| 4,552,759 | 11/1985 | Davis et al. ........................... 424/93 |
| 4,582,822 | 4/1986 | Hamill et al. ......................... 514/25 |
| 4,808,404 | 2/1989 | Bhogal .................................. 424/88 |

FOREIGN PATENT DOCUMENTS 1204057  5/1986  Canada .

OTHER PUBLICATIONS

Reid et al., "Effects of Monesin-Feeding Regimens on Flock Immunity to Coccidiosis", Poultry Science 56:66-71, 1977.

Ruff, M. D., Chute, M. B., and McLoughlin, D. K. "Resistance to Monensin Medication in *Eimeria tenella*," *Proc. Helminthol. Soc. Wash.*, 52(1), 1985, pp. 114-118.

Gordeuk, Jr., S., Bressler, G. O., and Glantz, P. J. "The Effect of Age of Bird and Degree of Exposure in the Development of Immunity to Cecal Coccidiosis in Chicks," *Poultry Sci.*, 30, 1951, pp. 503-506.

Long, P. L. "Observations on the duration of the acquired immunity of chickens to *Eimeria maxima* Tyzzer, 1929," *Parasitology*, 52, 1962, pp. 89-93.

Rose, M. E. "The early development of immunity to *Eimeria maxima* in comparison with that to *Eimeria tenella,*" *Parasitology*, 68, 1974, pp. 35-45.

Sanda, A. "Development of Immunity to Coccidiosis Caused by *Eimeria tenella* in One-day-old Chickens," *Acta vet. Brno*, 46, 1977, pp. 311-314.

Long, P. L., Johnson, J., and Wyatt, R. D. "*Eimeria tenella*: Clinical Effects in Partially Immune and Susceptible Chickens," *Poultry Sci.*, 59(10), 1980, pp. 2221-2224.

Long, P. L., Johnson, J., McKenzie, M. E., Perry, E., Crane, M. St. J., and Murray, P. K. "Immunisation of Yound Broiler Chickens with Low Level Infections of *Eimeria tenella, E. acervulina* or *E. maxima*," *Avian Path.*, 15, 1986, pp. 271-278.

Sharma, J. M., and Burmester, B. R. "Resistance to Marek's Disease at Hatching in Chickens Vaccinated as Embryos with the Turkey Herpesvirus," *Avian Diseases*, 26(1), 1982, pp. 134-149.

Jeffers, T. K. "Attenuation of Coccidia—A Review," presented at Georgia Coccidiosis Conference, Lake Lanier, GA, Nov. 17-21, 1985 (proceedings in press).

Farr, M. M., and Allen, R. W. "Sulfaguanidine Feeding as a Control Measure for Cecal Coccidiosis of Chickens," *Jour. A.V.M.A.*, 100, 1942, pp. 45-51.

Allen, R. W., and Farr, M. M. "Sulfaguanidine as a Prophylactic During the Period of Acquirement of Resistance by Chickens to Cecal Coccidiosis," *Am. Jour. Vet. Res.*, 4, 1943, pp. 50-53.

Seeger, K. C. "The Response of Induced and Natural *Eimeria tenella* Infections to Sulfaguanidine," *Proc. 49th Ann. Mtg. U.S. Livestock Sanitary Assn.*, 1945, pp. 45-47.

Swales, W. E. "New Methods of Controlling Caecal Coccidiosis in Chicks," *Canad. J. Comp. Med. Vet. Sci.*, 11(1), 1947, pp. 5-10.

Delaplane, J. F., Batchelder, R. M., and Higgins, T. C. "Sulfaquinoxaline in the Prevention of *Eimeria tenella* Infections in Chickens," *North Am. Vet.*, 28, 1947, pp. 19-24.

Grumbles, L. C., Delaplane, J. P., and Higgins, T. C. "Immunity Studies on *Eimeria tenella* Infection of Chickens in Relation to Sulfaquinoxaline Therapy," *Poultry Sci.*, 26, 1947, pp. 541-542.

Koutz, F. R. "Immunity Studies in Avian Cecal Coccidiosis. I. The Value of Drugs to Establish Immunity in Young Chickens," *Am. Jour. Vet. Res.*, 9, 1948, pp. 388-395.

Dickinson, E. M., Babcock, W. E., and Osebold, J. W. "Coccidial Immunity Studies in Chickens I," *Poultry Sci.*, 30, 1951, pp. 76-80.

Edgar, S. A., "Control of Cecal Coccidiosis by Active Immunization," *The Auburn Veterinarian*, Winter 1954, pp. 79-81 and 116.

Reid W. M. "The Relationship Between Coccidiostats and Poultry Flock Immunity in Coccidiosis Control Programs," *Poultry Sci.*, 39, 1960, pp. 1431-1437.

Rose, M. E. "Immunity." In: Hammond, D. M. and Long, P. L. (eds.), *The Coccidia* (Baltimore, University Park Press, 1973), pp. 295-341.

(List continued on next page.)

*Primary Examiner*—C. Fred Rosenbaum
*Assistant Examiner*—Sharon Rose
*Attorney, Agent, or Firm*—Kathleen R. S. Page; Leroy Whitaker

[57] ABSTRACT

The present invention is directed to an improved method for the control of coccidiosis, in which both ionophore chemotherapy and immunology are employed.

31 Claims, No Drawings

OTHER PUBLICATIONS

Sanda, A. "Vakcinace kurat proti kokcidióze,"-'*Veterinarstvi*, 32(8), 1982, pp. 366-367, (translation also included).

The Biology of the Coccidia, edited by Long (University Park Press, Baltimore, 1982) pp. 330-371, 473-475.

Sanda, V. A. "Immunprophylaxe der Kokzidiose bei Küken," *Mh. Vet.-Md.*, 40, 1985, pp. 165-167, (translation also included).

Smith II, C. K., Galloway, R. B., and White, S. L. "Effect of Inophores on Survival, Penetration, and Development of *Eimeria tenella* Sporozoites in Vitro," *J. Parasitol.*, 67(4), 1981, 511-516.

Doran, D. J., and Farr, M. M. "Susceptibility of 1- and 3-Day-Old Chicks to Infection with the Coccidium, *Eimeria acervulina*," *J. Protozool.*, 12(2), 1965, pp. 160-166.

COCCIVAC® Product Label and Information, Sterwin Laboratories, Inc.

Jeffers, T. K. Reduction of Anticoccidial Drug Resistance by Massive Introduction of Drug-Sensitive Coccidia, Avian Diseases 20(4), 649-653 (1976).

Long, P. L., et al. *Eimeria tenella:* Relative Survival of Drug-Resistant and Drug-Sensitive Populations in Floor Pen Chickens, Poultry Science 64, 2403-2405 (1985).

Polyether Antibiotics, edited by Westley (Marcell Dekker, Inc., New York, 1982) Chapter 6.

Monensin Symposium, Jun. 8-9, 1982, Eagle River, Ontario.

Augustine, et al., Poultry Science 66 (1987), pp. 960-965.

ANTICOCCIDIAL METHOD

This application is a continuation of application Ser. No. 06/901,912, filed 08/28/86, now abandoned.

BACKGROUND OF THE INVENTION

The present invention is directed to an improved method for the control of coccidiosis. The improvement resides in the discovery of a technique by which immunology can be employed in conjunction with ionophore chemotherapy.

Summary of the Invention

The present invention is directed to a method for protecting a coccidiosis-susceptible animal against coccidiosis which comprises (1) orally administering to the animal, at the neonate stage, infective coccidial organisms in a number effective to generate an immunological response by the animal, while (2) maintaining the animal free of any chemotherapeutic anticoccidial for a period beginning with birth or hatching and continuing after step (1) until sporozoites have penetrated host cells, and (3) thereafter administering an anticoccidially effective dose of an ionophore substantially continuously throughout the life of the animal.

The animals most susceptible to coccidiosis are the various fowl. Accordingly, a preferred embodiment of the present invention is the practice of the above method with fowl.

The use of the ionophore anticoccidials with fowl has been unusually successful, because only a very small number of strains of Eimeria (the protozoan pathogen which causes coccidiosis) exhibit reduced sensitivity or resistance to the ionophores. However, even this limited incidence of resistance presents a problem to the poultry industry. In addition to the loss in terms of reduced weight gain, poorer feed efficiency, and the like, coccidiosis of even a mild form can interfere with the uptake of pigmentation. The result is a bird that fails to meet the consumer's expectation for appearance. It is therefore another advantage that the present invention can be employed to control coccidiosis attributable to resistant strains of Eimeria.

Furthermore, it has been discovered that this control of resistant strains can be achieved by the administration of strains of Eimeria which are ionophore-sensitive, thereby minimizing the risk of further spread of resistance. Thus, in an especially preferred embodiment, the present invention is directed to a method of protecting a fowl against an ionophore-resistant strain of Eimeria which comprises (1) orally administering, to a newly-hatched fowl, an effective number of infective organisms of an ionophore-sensitive strain of Eimeria which is capable of conferring immunity against the ionophore-resistant strain of Eimeria, while (2) maintaining the fowl free of any chemotherapeutic anticoccidial for a period beginning with hatching and continuing after step (1) until sporozoites have penetrated host cells, and (3) thereafter administering an anticoccidially effective dose of an ionophore substantially continuously throughout the life of the fowl.

DETAILED DESCRIPTION OF THE INVENTION

The present invention is concerned with an improved therapy for coccidiosis. The invention makes use of the well-known class of anticoccidials, the ionophores, but provides improvement by using immunological methods of control of coccidiosis in addition to ionophore therapy.

The ionophores are a class of antibiotics of complex structure; from their inclusion of multiple oxygen atoms, they are also known as polyethers. Many members of this class are already known, and others are from time to time discovered. All ionophores exhibit anticoccidial activity, although the relative degree of such activity varies from ionophore to ionophore, and occasionally the toxicity of a particular ionophore may make its utilization as an anticoccidial impractical. Among the ionophores which have achieved significance for the commercial control of coccidiosis are monensin, narasin, lasalocid, and salinomycin. Any of these ionophores can be employed in the present invention. Other representative ionophores that can be used in the present invention include laidlomycin, nigericin, grisorixin, dianemycin, lenoremycin, lonomycin, antibiotic X206, alborixin, septamycin, antibiotic A204, etheromycin, isolasalocid, lysocellin, antibiotic A23187, maduramicin, A80190, and A80438.

The present improved method for controlling coccidiosis can be employed in any animal susceptible to coccidiosis. Although warm-blooded animals of all sorts are susceptible to coccidiosis, the fowl suffer most from coccidiosis; therefore, chemotherapeutic treatment by one of the ionophores is nearly universal. Chickens and turkeys are the species most commonly needing protection against coccidiosis, and because of their economic importance, the present invention is most useful for these species. However, the present invention can also be practiced with other species of fowl, such as duck, geese, quail, pheasants, and the like. Warm-blooded animals other than fowl are sometimes protected against coccidiosis by use of the same ionophores utilized with fowl. The present improved method can therefore be used with such other species, such as cattle, sheep, swine, and the like.

The present invention is carried out by administering infective coccidial organisms to an animal susceptible to coccidiosis. The administration is carried out at the neonate stage, shortly after birth or hatching. In general, the administration will be carried out within the first 24 hours from birth or hatching. In typical poultry practices, each fowl is handled shortly after hatching, generally within the first 6 to 12 hours after hatching. In this handling, the fowl is typically debeaked, and vaccinated against various diseases, notably Marek's disease, infectious bronchitis, Newcastle's disease, and the like. In other poultry species, the birds are not handled individually or debeaked, but are nonetheless treated at this neonate stage by exposure to an aerosol which delivers the necessary vaccines against the same disease.

It has been found that the present invention can conveniently be practiced as part of these standard procedures, and indeed, that certain time relationships must be observed to obtain the benefits of the present invention. Various references suggest that a newly hatched fowl is incapable of a full immunogenic response. However, the inventors have found that vaccination at the neonate stage is indeed effective, and, when employed in conjunction with the earliest possible use of ionophores consistent with the immunological process, provides superior control of coccidiosis.

In accordance with the present invention, infective coccidial organisms are administered to the animal to be protected against coccidiosis. The exact form of the organisms is not critical, so long as the form is one which will generate an immunological response by the animal. Suitable forms of infective coccidial organisms include sporulated oocysts, sporozoites, and sporocysts. Both of the latter forms require additional workup, and sporozoites are relatively unstable. Generally, the preferred form will be sporulated oocysts. The preparation of suspensions of various forms of infective coccidial organisms is well known to those skilled in the art. A representative preparation of sporulated oocysts is shown below in Example 1.

It is important that the infective coccidial organisms be administered orally. Again, the objective is an immunological response by the animal, and administration by other routes is less certain to engender the necessary immunological response. Oral administration is also desirable in that the precise number of infective organisms can be controlled. For these various reasons, the present invention is generally practiced by spraying a suspension containing the necessary coccidial organisms directly into the animal's mouth. However, in accordance with other practices described above, oral administration can also be achieved by aerosol delivery. It is known that aerosol delivery is an indirect mode of delivery to the mouth cavity. Material which the bird absorbs from an aerosol ocularly or nasally will in part drain to the mouth cavity; also, material deposited from an aerosol onto the bird's feathers will, by means of preening, also arrive at the bird's mouth cavity. Therefore, although the present invention is directed to oral administration, this term includes aerosol delivery which inevitably becomes an oral administration.

Although it is possible that the infective organisms can be administered in more than one dose, there is no advantage to multiple dosings, and multiple dosings have the effect of delaying ionophore therapy. In practice, one single dose is much preferred.

The exact number of infective coccidial organisms to be administered is not critical except that the number must be effective to engender an immunological response by the animal. In general, an immunological response can be obtained when using from 1 to 100,000 oocysts. The exact number can be determined by those of ordinary skill in the art, by the use of simple range-finding experiments. The exact number will vary with the species and size of the particular animal, the relative immunogenicity of the particular strain which is sought to be controlled, whether the strain is a wild strain or an attenuated strain, and other factors known to those skilled in the art. In many cases, good results are obtained in fowl with single doses of from about 10 to about 5,000 oocysts of *Eimeria maxima* or *Eimeria tenella*, and with single doses of from about 50 to about 20,000 oocysts of *Eimeria acervulina*. In some situations, doses of from 1,000 to 5,000 oocysts of *Eimeria maxima* and *Eimeria tenella*, and from 5,000 to 10,000 oocysts of *Eimeria acervulina* will suffice.

In a preferred embodiment, the present invention is used to control coccidiosis attributable to Eimeria strains which are not controlled by the ionophores. In this embodiment, the present invention provides better anticoccidial protection than is possible by the use of the ionophores, alone. A number of strains of Eimeria are known to exhibit reduced sensitivity, or even outright resistance, to the ionophores. In the use of the present invention for the control of such strains, the immunizing dose of infective coccidial organisms can be of the very strain sought to be controlled, that is, the strain exhibiting reduced sensitivity or resistance. However, the propagation of ionophore-resistant organisms runs the risk of increasing the incidence of such organisms in the general Eimeria population. It is therefore preferred to use an ionophore-sensitive strain which will confer immunity against the ionophore-resistant strain. In general, different strains of the same species will confer immunity against other strains of the same species. However, this is not universally true, so that in practice, it will be appropriate to determine whether a particular ionophore-sensitive strain is, indeed, capable of conferring immunity against the ionophore-resistant strain sought to be controlled.

This can be determined by simple preliminary tests easily within the skill of the ordinary artisan. Generally, the test is conducted by administering the candidate ionophore-sensitive strain, withholding all anticoccidial chemotherapy, and shortly thereafter, such as from 5 to 20 days, challenging the birds with the ionophore-resistant strain sought to be controlled. The birds are then sacrificed and the usual parameters of coccidiosis disease evaluated. However, it is also possible to follow the immunological response of the birds by ascertaining the levels of antibodies. By these techniques, one can determine in a small scale test whether a particular ionophore-sensitive strain of Eimeria will confer immunity on the ionophore-resistant strain sought to be controlled.

After the step of administering the infective coccidial organisms, it is necessary that there be a delay until ionophore chemotherapy is begun. The function of the delay is to permit the immunological process to proceed, uninterrupted. The delay must therefore be long enough to permit the infective coccidial organisms to travel to the relevant section of the intestinal tract and invade host cells, after which the immunological process will proceed because the intracellular organisms are protected from ionophore therapy. The exact number of hours of delay will vary with the identity of the host and the rate of transit through the gastrointestinal tract; and with the particular species of coccidium and the location of the gastrointestinal tract which it infects. Much is known by those skilled in the art concerning normal transit times through the gastrointestinal tract, the site of infection by the various coccidial species, and the like. In chickens, this delay should be on the general order of one to four hours. In cattle, it is expected that the delay will be on the order of 4–8 hours. It is possible to delay chemotherapeutic treatment for an even longer time period, such as up to 24 hours. However, further delay leaves the animal unprotected from coccidiosis, except as has been provided by the immunological process, and is therefore undesirable. The preferred practice, therefore, is to delay ionophore therapy only as long as the time required for sporozoites to penetrate host cells.

Following this delay period, ionophore therapy is begun and is employed substantially continuously throughout the life of the animal. As noted above, many of the ionophores are used commercially for the control of coccidiosis. Those of ordinary skill in the art are therefore well acquainted with the techniques for their use, the amounts thereof which are effective to control coccidiosis, and the like, so that a detailed discussion is not needed. Effective anticoccidial amounts for several of the ionophores, expressed in terms of the concentration in the feedstuff, are monensin 80 to 125 ppm
narasin 50 to 80 ppm
lasalocid 75 to 125 ppm
salinomycin 40 to 70 ppm
maduramicin 4 to 8 ppm
A80190 10 to 40 ppm Although the ionophore is to be administered substantially continuously throughout the life of the animal, occasional interruptions and pre-slaughter withdrawal do not alter the advantages of the present invention.

Typically the ionophore therapy required by the present invention will be achieved by using a single ionophore as the sole anticoccidial agent. However, it is entirely possible to use a mixture of two ionophores, in which case the amounts of each will be reduced.

All of the foregoing teaching is based on present conventional practices for the rearing of animals, especially those practices for the rearing of poultry, which suffer the most from coccidiosis. However, the present invention is also adapted to be employed in conjunction with newly emerging technology for the embryonic immunization of poultry. Attention is directed to U.S. Pat. No. 4,458,630, and to *Avian Diseases* 26(1):134–149, 1982. In embryonic immunization, an immunizing substance is injected into avian eggs. The present invention can be adapted for use in conjunction with embryonic immunization. In this adaptation, the immunization necessary to the present invention is carried out in accordance with U.S. Pat. No. 4,458,630, except that it is not believed to be necessary for the present invention that oocysts be injected into the amnion or the yolk sac. Rather, it is believed that embryonic immunization against coccidiosis can also be achieved by injection into the chorioallantoic cavity.

After hatching, the practice of the present invention is the same, that is, an anticoccidially effective dose of an ionophore is administered substantially continuously throughout the life of the bird. However, the exact timing of immunological response to embryonic immunization is not known with certainty; the response may in fact be delayed until hatching, when the yolk sac is absorbed and becomes a part of the intestinal tract of the bird. Furthermore, the immunological response may vary some from egg to egg, depending on the exact site of injection. Therefore, to assure maximum response to embryonic immunization, the ionophore therapy is preferably delayed, even as in the main embodiment of the present invention. With embryonic immunization, the delay period should be determined by the same factors discussed above, but calculated as if hatching were the point of exposure to infective coccidial organisms.

In this adaptation, then, the present invention is directed to a method for protecting a fowl against coccidiosis which comprises (1) during the final quarter of an incubation period of an avian egg comprising an embryo, injecting the egg with infective coccidial organisms in a number effective to generate an immunological response, and (2) following hatching, administering an anticoccidially effective dose of an ionophore substantially continuously throughout the life of the fowl.

In this adaptation of the present invention as in the general practice of the invention, another preferred embodiment is the use of an ionophore sensitive strain of Eimeria to protect against an ionophore resistant strain of Eimeria.

The present invention is illustrated by the following examples.

EXAMPLE 1

Preparation of Sporulated Oocyst Suspension

Source

A suspension of sporulated oocysts suitable for carrying out the present invention was prepared as described below.

The coccidial strain employed was *Eimeria maxima* FS-177 (ATCC, Rockville, Md. 20852, deposit #40357 on Aug. 4, 1987), which was originally isolated in 1974 from Perdue Farms, Inc., Salisbury, Md. Since its isolation, it has been maintained by passage through chickens. The strain is ionophore sensitive.

Production of Oocysts

An infectious inoculum was prepared by diluting a stock suspension of sporulated oocysts to the appropriate concentration (15,000–50,000 oocysts/ml) with tap water.

Birds were inoculated with the culture via crop intubation using a syringe. Between 15,000 and 50,000 *Eimeria maxima* oocysts were administered to each bird in not more than 1 ml of solution.

The birds were housed in steam-sterilized battery cages for eight days post infection. Other special precautions were employed. The birds were monitored for the eight-day prepatent period. Fecal material was microscopically examined for the presence of oocysts other than *Eimeria maxima*. In addition, the intestinal tracts of all birds were later examined for the presence of lesions produced by other coccidial species (Johnson and Reid, 1970).

On the seventh and eighth days post infection, the feces from these birds were collected and blended with tap water to obtain a homogeneous suspension of oocysts.

Workup

This suspension was strained through a fine mesh screen so that all particulate material was removed. The resultant suspension was then added to an equal volume of saturated NaCl in order to separate the oocysts from the remaining fecal debris (although NaCl was used in this workup, any other additive which creates a high viscosity solution can be used instead of NaCl; other additives commonly employed are sucrose and $ZnSO_4$). The oocysts floated to the surface of the NaCl solution and were collected via aspiration. The oocysts were then washed free of the saturated salt by repeated low-speed centrifugation. (Large quantities of purified oocysts may be produced via continuous flow centrifugation, see Vetterling, J. M., *J. Parasitol.* 55:412–417, 1969.)

A concentrated aggregate of oocysts produced as described above was mixed into 2% $K_2Cr_2O_7$ (potassium dichromate) to cause the oocysts to sporulate. The number of sporulated oocysts in a solution was determined microscopically by counting the number of infective organisms which appeared on the grid of a hemacytometer. When the number of sporulated oocysts/ml had been determined, dilutions with 2% $K_2Cr_2O_7$ were made to the desired concentration of sporulated oocysts/ml. Determinations of purity and potency were performed by microscopic examination of oocyst morphology. The number of sporulated oocysts/ml in each lot was verified.

EXAMPLE 2

The Effect of Day-Old Immunization With *Eimeria maxima* on the Response to Challenge Infection at 10 Days of Age cally equivalent to the nonimmunized, nonchallenged controls.

The results of this study indicate that the day-old chick is capable of mounting a protective immune response after an initial immunizing dose of 2,000 sporulated *Eimeria maxima* oocysts. This protective effect was observed in performance, lesion scores, oocyst output and serum $\beta$-carotenoid equivalents seven days after a severe challenge inoculation.

TABLE 1

| | Parameters of Coccidiosis[1] | | | | | |
|---|---|---|---|---|---|---|
| Group | % Mortality | Average Weight Gain | F/G | Lesion Scores (0 = none, 4 = maximum) | Total oocysts/bird | Serum $\beta$-carotenoid equivalents ($\mu$g/ml) |
| Nonimmunized, nonchallenged | 0[a] | 385.7[a] | 1.574[b] | 0[c] | 0[b] | 5.23[a] |
| Nonimmunized, challenged on day 10 | 0[a] | 287.7[b] | 1.911[a] | 4.00[a] | 42,430,000[a] | 1.09[b] |
| Immunized, challenged on day 10 | 0[a] | 314.9[b] | 1.660[b] | 0.65[b] | 500,000[b] | 4.13[a] |

[1]Means within columns not followed by a common letter are significantly different $P < 0.05$.

A battery experiment was performed with Hubbard chicks to evaluate the effects of day-old immunization with *Eimeria maxima* (FS-177 strain) on the response to challenge by the same species and strain at ten days of age. No ionophore was employed in this experiment.

Hubbard-White Mountain cockerels were used in this experiment. Immediately after delivery from the hatchery, birds were weighed and assigned to treatment groups. Each treatment was replicated five times and each replicate contained four chicks. Chicks were fed a standard broiler starter ration for the duration of the experiment. The treatments used in the study were:

1. Nonimmunized, nonchallenged.
2. Nonimmunized, challenged on day 10.
3. Immunized day 0, challenged on day 10.

Immunized birds were orally inoculated with 2,000 *Eimeria maxima* oocysts on day 0. The inoculation was with a suspension of sporulated oocysts prepared as described in Example 1. Those groups which were challenged were orally administered 50,000 *Eimeria maxima* (FS-177 strain) oocysts/bird on day 10.

Seven days after the administration of the challenge inoculum, all birds were weighed, bled via cardiac puncture and lesion scored (J. Johnson and W. M. Reid, *Exp. Parasitol.* 28:30–36, 1970). Serum was prepared from each blood sample and analyzed for $\beta$-carotenoid equivalents (Ruff et al., *Poultry Sci.* 53:1801–1809, 1974). In addition, feces from all groups were collected on days 6 and 7 post challenge. From this material, average oocyst production per bird was ascertained.

The results of this trial are presented in Table 1. Challenge infection administered on day 10 produced significant reductions in performance and $\beta$-carotenoid equivalents of birds not protected by immunization on day 0. This was accompanied by a severe mean intestinal lesion score and an oocyst output over 40 million/bird.

Birds immunized with 2,000 *Eimeria maxima* oocysts on day 0, however, experienced significant improvement in feed conversion and numerical increases in weight gain when compared to nonimmunized/challenged birds. Likewise, lesion scores and oocyst output were dramatically reduced by the immunization regimen and, as a result, serum pigmentation was statisti-

EXAMPLE 3

The Effect of Day-Old Immunization With *Eimeria maxima* on the Response to Challenge at 21 Days of Age, in Conjunction with Monensin A floor pen study was conducted with Hubbard straight-run chickens to assess the effects of day-old immunization with *Eimeria maxima* strain FS-177 on the response to challenge by *Eimeria maxima* FS-410 (an ionophore resistant strain) at 21 days of age. In addition, the effects of monensin (100 ppm) on these immunization schemes were determined in a complete 2×2 factorial design.

The results of this experiment indicate that oral immunization (2,000 *Eimeria maxima* strain FS-177 oocysts) protected birds from challenge of *Eimeria maxima* strain FS-410 at 21 days when lesion scores and serum pigmentation were evaluated. This phenomenon occurred in both the presence and absence of 100 ppm of monensin.

Hubbard-white Mountain straight-run chickens were used in this test. Immediately after delivery from the hatchery birds were randomly assigned to treatment groups. Each treatment was replicated four times and contained 50 birds per replicate. Chicks were fed a standard broiler starter ration which contained either 0 or 100 ppm monensin for the duration of the experiment. The treatments used in this study were:

1. Nonmedicated, nonimmunized.
2. Nonmedicated, immunized (2,000 *Eimeria maxima* strain FS-177 oocysts).
3–4. As 1–2 with 100 ppm monensin incorporated into broiler feed.

Immunized birds were orally inoculated with 2,000 *Eimeria maxima* (FS-177) oocysts approximately four hours before they were fed either the nonmedicated ration or the medicated ration. The inoculation was with a suspension of sporulated oocysts prepared as described in Example 1. All birds were challenged on day 21 by spreading infectious litter containing oocysts of *Eimeria maxima* (FS-410) over the existing litter in the floor pen. Seven days post challenge, all birds were weighed and sacrificed, and 15 birds per replicate were chosen at random for lesion scoring and serum pigmentation analysis. The techniques of Johnson and Reid (*Exp. Parasitol.* 28:30–36, 1970) were used to evaluate lesion scores, while the methods of Ruff et al., (*Poultry Sci.,* 53:1801–1809, 1974) were employed in pigmentation analyses.

Data were analyzed using analysis of variance (ANOVA) procedures; in some cases differences between treatment means were determined using Student-Newman-Keul's test (P<0.05).

The results of this study are presented in Table 2. Birds immunized with 2,000 *Eimeria maxima* oocysts were protected from challenge infection (FS-410) at 21 days of age when lesion scores and serum pigmentation were evaluated. Similar trends were observed in immunized birds which were fed monensin.

The results of this study indicate that immunized chicks raised in floor pens mount an immune response which is capable of protecting them from the adverse effects of an ionophore resistant challenge at 21 days of age. Significant improvements in lesion scores and serum pigmentation illustrate the protective effects of oral immunization on the first day of life.

The results of the study revealed that day-old immunization with *Eimeria maxima* protected birds from challenge at 1 day of age when weight gain was analyzed. Inconsistent results in lesion scores and serum pigmentation indicated that the challenge in the litter may have been insufficient to fully evaluate the effects of immunization on lesion scores and serum pigmentation.

Hubbard-white Mountain straight-run broiler chickens were used in this study. Immediately after delivery from the hatchery, birds were randomly assigned to treatment groups; each treatment was replicated four times and contained 50 birds per replicate. Chicks were fed a standard broiler starter ration for the duration of the test. The treatments used in this study were:

1. Nonmedicated, nonimmunized.
2. Nonmedicated, immunized (2000 *Eimeria maxima* FS-177 oocysts).
3. Nonmedicated, immunized (2000 *Eimeria maxima* FS-177 oocysts) +levamisole (5 mg/kg body weight) days 4, 5 and 6 in drinking water.
4–6. As 1–3 with 100 ppm monensin incorporated into feed.

TABLE 2

The Effect of Day-Old Immunization with *Eimeria maxima* FS-177
on Response to Challenge by *Eimeria maxima* FS-410
at 21 Days of Age in Floor Pens
Results[1]

| | Monensin Concentration | | | | | |
|---|---|---|---|---|---|---|
| | 0 ppm | | | 100 ppm | | |
| Immunization | Ave. Wt. Gain (g) | Average Intestinal Lesion Score | $\beta$-carotene equivalents ($\mu$g/ml of serum) | Ave. Wt. Gain (g) | Average Intestinal Lesion Score | $\beta$-carotene equivalents ($\mu$g/ml of serum) |
| No | 970$^a$ | 2.90$^a$ | 2.45$^b$ | 943$^a$ | 2.03$^a$ | 3.43$^{ab}$ |
| Yes | 978$^a$ | 0.80$^b$ | 3.96$^a$ | 950$^a$ | 0.93$^b$ | 3.98$^a$ |

[1]Means within columns not followed by a common letter are significantly different P < 0.05.

ANOVA - One Way

| Source | SS | DF | MS | F-Ratio |
|---|---|---|---|---|
| Treatment | 10.2744 | 5 | 2.0548 | 5.376 |
| Error | 6.8794 | 18 | 0.3821 | |
| Total | 17.1539 | 23 | | |

(Pooled standard error of the mean for weight gain, lesion scores, and $\beta$-carotene equivalents were 12.6, 0.26, and 0.31, respectively.)

EXAMPLE 4

The Effect of Day-Old Immunization with *Eimeria maxima* on the Response to Continuous Challenge, in Conjunction with Monensin A floor pen experiment was conducted with Hubbard straight-run chickens to assess the effects of day-old immunization with *Eimeria maxima* FS-177 on the response to challenge by *Eimeria maxima* FS-410 beginning shortly after immunization. The challenge was provided by reusing the same floor pens and litter from the experiment reported in Example 3. In addition, the effects of levamisole administration in drinking water (5 mg/kg body weight) and monensin (100 ppm) in the feed were also evaluated in a 3×2 factorial experimental design.

Immunized birds were orally inoculated with 2000 *Eimeria maxima* (FS-177) oocysts approximately four hours before being placed on either the medicated or nonmedicated ration. The inoculation was with a suspension of sporulated oocysts prepared as described in Example 1. Levamisole, a substance reported to enhance the immune response, was mixed into drinking water during days 4, 5 and 6 at a concentration of 5 mg/kg body weight. The litter upon which all birds were placed on day 1 contained oocysts of *Eimeria maxima* FS-410.

On day 21, fifteen birds from each pen were selected at random, bled via cardiac puncture and lesion scored according to the procedures of Johnson and Reid (*Exp. Parasitol.* 28:30–36, 1970). Serum was prepared and analyzed for $\beta$-carotenoid equivalents (Ruff et al., *Poultry Sci.* 53:1801–1809, 1974). On day 28 the experiment was completed and performance criteria were determined.

Data were analyzed using analysis of variance (ANOVA); differences between treatment means were evaluated using Student-Newman-Keul's test (P<0.05).

The results are presented in Table 3 and indicate that immunization produced significant improvements in performance when compared to nonimmunized, nonmedicated controls. Generally, lesion scores were not severe on day 21; serum pigmentation values were inconsistent and demonstrated no trends of treatment effects, due to insufficient coccidial challenge.

TABLE 3

The Effect of Day-Old Immunization with *Eimeria maxima* on the Response to Continuous Challenge in Floor Pens[1]

| | Monensin Concentration | | | | | |
|---|---|---|---|---|---|---|
| | 0 ppm | | | 100 ppm | | |
| Immunization | Wt. Gain (g) | Lesion Score | $\beta$-CE[2] | Wt. Gain (g) | Lesion Score | $\beta$-CE[2] |
| None | 738[b] | 0.12[a] | 4.34[ac] | 806[a] | 0.25[a] | 4.51[ab] |
| Oral[3] | 786[a] | 0.00[a] | 3.39[c] | 804[a] | 0.25[a] | 5.26[a] |
| Oral + Levamisole[4] | 814[a] | 0.50[a] | 3.55[bc] | 794[a] | 0.25[a] | 4.86[a] |

[1] Means within columns not followed by a common letter are significantly different. Each treatment contained four replicates of 50 straight-run chicks. Lesion scores and blood parameters were collected on day 21.
[2] $\beta$-carotenoid equivalents in μg/ml.
[3] Oral immunization contained 2,000 *Eimeria maxima* oocysts on day 0.
[4] Oral + levamisole treated birds were immunized with 2,000 *Eimeria maxima* oocysts on day 0 and given levamisole (5 mg/kg body weight) in the drinking water on days 4, 5 and 6 of the experiment.

| ANOVA - One Way | | | | |
|---|---|---|---|---|
| Source | SS | DF | MS | F-Ratio |
| Treatment | 10.6672 | 5 | 2.1334 | 7.199 |
| Error | 5.3336 | 18 | 0.2963 | |
| Total | 16.0009 | 23 | | |

(Pooled standard error of the mean for weight gain, lesion scores, and $\beta$-carotene equivalents were 27.7, 0.24, and 0.27, respectively.)

EXAMPLE 5

Larger Floor Pen Study

A larger floor pen study was conducted in which each treatment consisted of eight pens, with 130 birds per pen. There were intended to be four treatments:

nonimmunized, nonmedicated
immunized, nonmedicated
nonimmunized, medicated with monensin, 120 ppm
immunized, medicated with monensin, 120 ppm However, because of a mixing error, for the first 21 days of the trial all birds were medicated (monensin, 120 ppm). Thereafter, the birds were treated exactly as listed above. The trial was carried through an entire grow out period (47 days). This study was done at a location generally contaminated with strains of *Eimeria maxima* resistant to monensin.

The immunizing oocysts were *Eimeria maxima* FS-177, prepared as described above in Example 1. The oocysts were administered orally by a Beak-O-Vac machine (sold by Beak-O-Vac, Inc., P.O. Box 715, Gainesville, Ga. 30501), approximately two hours before the birds were placed on feed.

Various parameters of anticoccidial efficacy were evaluated:

(1) On day 16, ten birds/pen were removed and challenged with 50,000 oocysts of *Eimeria maxima* FS-410; seven days later (day 23) the birds were bled and sacrificed. Lesion scores and serum $\beta$-carotenoid equivalents were determined.

(2) Body weight and feed conversion of the remaining birds were determined at day 21.

(3) On each of days 27, 34, 41, and 47, five birds/pen were bled and serum $\beta$-carotenoid equivalents were determined.

(4) At the end of the 47-day period, body weight, final feed conversion, and processing and carcass characteristics were determined for all remaining birds.

Results and statistical analyses were as set forth in the following four tables. Lesion scores were rated on a scale of 0–4, with 0=no lesions and 4=a maximum number of lesions. In the tables, "Serum $\beta$-carotenoid equivalents" is abbreviated to "Serum $\beta$-CE"; the "Analysis of Variance" statistical analysis is abbreviated to "ANOVA"; and the pooled standard error of the mean is abbreviated to PSEM.

TABLE 4

Data on Birds Challenged at Day 16, Sacrificed at Day 23

| Treatment* | Lesion Scores | Serum $\beta$-CE (μg/ml) |
|---|---|---|
| Immunized + Monensin | 2.25 | 2.39 |
| Immunized + Monensin | 2.17 | 2.37 |
| Monensin | 3.44 | 1.94 |
| Monensin | 3.46 | 1.73 |

*A mean was calculated for each of the four groups prior to discovery of the mixing error.

| ANOVA (Lesion Scores) | | | | | |
|---|---|---|---|---|---|
| SOV | df | SS | MS | F | P |
| Total | 31 | 26.200300 | | | |
| Trt | 3 | 12.327325 | 4.1091083 | 8.3 | <.001 |
| Immunized (I) | 1 | 12.3008000 | | 24.8269 | <.001 |
| Monensin (M) | 1 | 0.0055125 | | <1 | NS |
| (I × M) | 1 | 0.0210125 | | <1 | NS |
| Error | 28 | 13.872975 | 0.4954634 | | |

PSEM = 0.25

| ANOVA (Serum $\beta$-CE) | | | | | |
|---|---|---|---|---|---|
| SOV | df | SS | MS | F | P |
| Total | 31 | 7.6563969 | | | |
| Trt | 3 | 2.5643344 | 0.8547781 | 4.7 | <.01 |
| Immunized (I) | 1 | 2.3925781 | | 13.16 | <.005 |
| Monensin (M) | 1 | 0.1023781 | | <1 | NS |
| I × M | 1 | 0.0693781 | | <1 | NS |
| Error | 28 | 5.0920625 | 0.1818594 | | |

PSEM = 0.15

TABLE 5

Performance Data on Remaining (Non Challenged) Birds at Day 21

| Treatment | Body Weight (lbs.) | Feed Conversion |
|---|---|---|
| Immunized + Monensin | 1.273 | 1.458 |
| Monensin | 1.277 | 1.465 |

| ANOVA (Body Weight, 21 Days) | | | | | |
|---|---|---|---|---|---|
| SOV | df | SS | MS | F | P |
| Total | 31 | 0.0111962 | | | |
| Trt | 1 | 0.0001575 | | <1 | NS |

-continued

ANOVA (Body Weight, 21 Days)

| SOV | df | SS | MS | F | P |
|---|---|---|---|---|---|
| Error | 30 | 0.0110387 | 0.000368 | | |

PSEM = 0.005

ANOVA (Feed Conversion, 21 Days)

| SOV | df | SS | MS | F | P |
|---|---|---|---|---|---|
| Total | 31 | 0.0087122 | | | |
| Trt | 1 | 0.0003445 | | 1.235 | NS |
| Error | 30 | 0.0083677 | 0.0002789 | | |

PSEM = 0.004

TABLE 6

Weekly β-Carotenoid Equivalents (μg/ml)

| Treatment | Day 27 | Day 34 | Day 41 | Day 47 |
|---|---|---|---|---|
| Immunized + Monensin | 17.32 | 19.26 | 25.44 | 27.96 |
| Immunized | 16.09 | 17.65 | 22.71 | 26.94 |
| Monensin | 15.73 | 18.19 | 24.63 | 28.42 |
| Control | 14.54 | 15.43 | 24.03 | 22.36 |

ANOVA (Day 27)

| SOV | df | SS | MS | F | P |
|---|---|---|---|---|---|
| Total | 31 | 427.35745 | | | |
| Trt | 3 | 31.575434 | | | |
| Immunized (I) | 1 | 19.797778 | | 1.401 | NS |
| Monensin (M) | 1 | 11.773378 | | .833 | NS |
| I × M | 1 | 0.004278 | | <1 | NS |
| Error | 28 | 395.78202 | 14.135072 | | |

PSEM = 1.32

ANOVA (Day 34)

| SOV | df | SS | MS | F | P |
|---|---|---|---|---|---|
| Total | 31 | 262.029670 | | | |
| Trt | 3 | 62.433109 | 20.811036 | 2.919 | .05 |
| Immunized (I) | 1 | 21.598878 | | 3.03 | .075 |
| Monensin (M) | 1 | 38.171953 | | 5.35 | .025 |
| I × M | 1 | 2.6622781 | | <1 | NS |
| Error | 28 | 199.59656 | 7.1284486 | | |

PSEM = 0.9

ANOVA (Day 41)

| SOV | df | SS | MS | F | P |
|---|---|---|---|---|---|
| Total | 31 | 254.01399 | | | |
| Trt | 3 | 31.679838 | 10.559946 | 1.329 | NS |
| Immunized (I) | 1 | 0.5253125 | | <1 | NS |
| Monensin (M) | 1 | 22.144513 | | 2.7888 | NS |
| I × M | 1 | 9.0100125 | | 1.1346901 | NS |
| Error | 28 | 222.33415 | 7.9405054 | | |

PSEM = 0.996

ANOVA (Day 47)

| SOV | df | SS | MS | F | P |
|---|---|---|---|---|---|
| Total | 31 | 498.2835 | | | |
| Trt | 3 | 184.70868 | | 5.50 | <.005 |
| Immunized (I) | 1 | 33.763653 | | 3.01 | <.10 |
| Monensin (M) | 1 | 100.2174 | | 8.95 | <.01 |
| I × M | 1 | 50.727628 | | 4.53 | <.05 |
| Error | 28 | 313.57482 | 11.199101 | | |

PSEM = 2.5

TABLE 7

Final Performance Data (47 Days)*

| Treatment | Body Weight (lbs.) | Final Feed Conversion | Processing and Carcass Characteristics** Color % 1-2 | Finish % 1-2 |
|---|---|---|---|---|
| Immunized + Monensin | 4.632$^b$ | 1.953 | 92.05 | 100 |
| Immunized | 4.755$^a$ | 1.956 | 94.45 | 100 |
| Monensin | 4.651$^{ab}$ | 1.956 | 95.00 | 100 |
| Control | 4.696$^{ab}$ | 1.977 | 87.00 | 98.9 |

*Means within columns not followed by a common letter are significantly different.
**Each processed bird was given a score ranging from 1-5 for color and finish, with 1-2 = very good to excellent and 3-4 = fair to good.

ANOVA (Final Body Weight)

| SOV | df | SS | MS | F | P |
|---|---|---|---|---|---|
| Total | 31 | 0.237622 | | | |
| Trt | 3 | 0.0682438 | 0.0227479 | | |
| Immunized (I) | 1 | 0.0018911 | | <1 | NS |
| Monensin (M) | 1 | 0.0510401 | | 8.44 | <.01 |
| I × M | 1 | 0.0153125 | | 2.53 | NS |
| Error | 28 | 0.1693782 | 0.0060492 | | |

PSEM = 0.03

ANOVA (Final Feed Conversion)

| SOV | df | SS | MS | F | P |
|---|---|---|---|---|---|
| Total | 31 | 0.0112202 | | | |
| Trt | 3 | 0.0029266 | 0.0009755 | 3.29 | <.05 |
| Immunized (I) | 1 | 0.0011400 | | 3.85 | <.075 |
| Monensin (M) | 1 | 0.0010928 | | 3.69 | <.075 |
| I × M | 1 | 0.0006938 | | 2.34 | NS |
| Error | 28 | 0.0082936 | 0.0002962 | | |

PSEM = 0.006

We claim:

1. A method for protecting a coccidiosis-susceptible animal against coccidiosis which comprises
    (1) orally administering to the animal, at only the neonate stage, infective coccidial organisms in a number effective to generate an immunological response by the animal, while
    (2) maintaining the animal free of any chemotherapeutic anticoccidial for a period beginning with birth or hatching and continuing after step (1) until sporozoites have penetrated host cells, and
    (3) thereafter administering an anticoccidially effective dose of an ionophore substantially continuously throughout the life of the animal.

2. The method of claim 1 wherein the coccidiosis-susceptible animal is a swine.

3. The method of claim 2 wherein the ionophore is monensin.

4. The method of claim 1 wherein the coccidiosis-susceptible animal is a sheep.

5. The method of claim 4 wherein the ionophore is monensin.

6. The method of claim 1 wherein the coccidiosis-susceptible animal is a bovine.

7. The method of claim 6 wherein the ionophore is monensin.

8. The method of claim 1 wherein the coccidiosis-susceptible animal is a fowl.

9. The method of claim 8 wherein the ionophore is monensin.

10. The method of claim 8 wherein the ionophore is lasalocid.

11. The method of claim 8 wherein the ionophore is narasin.

12. The method of claim 8 wherein the ionophore is salinomycin.

13. The method of claim 8 wherein the ionophore is maduramicin.

14. The method of claim 8 wherein the ionophore is A80190.

15. The method of claim 8 wherein the ionophore is A80438.

16. A method for protecting a fowl against coccidiosis attributable to an ionophore-resistant strain of Eimeria which comprises
   (1) orally administering to the fowl, only within 24 hours of hatching, an effective number of infective organisms of an ionophore-sensitive strain of Eimeria which is capable of conferring immunity against the ionophore-resistant strain of Eimeria, while
   (2) maintaining the fowl free of any chemotherapeutic anticoccidial for a period beginning with hatching and continuing after step (1) until sporozoites have penetrated host cells, and
   (3) thereafter administering an anticoccidially effective dose of an ionophore substantially continuously throughout the life of the fowl.

17. The method of claim 16 wherein the ionophore is monensin.

18. The method of claim 16 wherein the ionophore is lasalocid.

19. The method of claim 16 wherein the ionophore is narasin.

20. The method of claim 16 wherein the ionophore is salinomycin.

21. The method of claim 16 wherein the ionophore is maduramicin.

22. The method of claim 16 wherein the ionophore is A80190.

23. The method of claim 16 wherein the ionophore is A80438.

24. The method of claim 16 wherein the ionophore-resistant strain of Eimeria is an ionophore-resistant strain of *Eimeria maxima*.

25. The method of claim 24 wherein the ionophore is monensin.

26. The method of claim 24 wherein the ionophore is lasalocid.

27. The method of claim 24 wherein the ionophore is narasin.

28. The method of claim 24 wherein the ionophore is salinomycin.

29. The method of claim 24 wherein the ionophore is maduramicin.

30. The method of claim 24 wherein the ionophore is A80190.

31. The method of claim 24 wherein the ionophore is A80438.

* * * * *